United States Patent [19]

Davis et al.

[11] Patent Number: 4,846,804

[45] Date of Patent: Jul. 11, 1989

[54] COMBINED NEEDLE PROTECTOR AND GUIDEWIRE FEEDER

[75] Inventors: Richard E. Davis, Wyoming; Ronald A. DeVries, Zeeland, both of Mich.

[73] Assignee: DLP Inc., Grand Rapids, Mich.

[21] Appl. No.: 172,477

[22] Filed: Mar. 24, 1988

[51] Int. Cl.[4] ............................................. A61M 5/00
[52] U.S. Cl. ................................ 604/164; 604/197; 604/263
[58] Field of Search ........................... 604/164–170, 604/197, 263

[56] References Cited

U.S. PATENT DOCUMENTS

| | | | |
|---|---|---|---|
| 3,352,306 | 11/1967 | Hirsch | 604/164 |
| 4,721,506 | 1/1988 | Teves | 604/164 |
| 4,772,267 | 9/1988 | Brown | 604/263 X |

Primary Examiner—Stephen C. Pellegrino
Attorney, Agent, or Firm—Barnes, Kisselle, Raisch, Choate, Whittemore & Hulbert

[57] ABSTRACT

A combined percutaneous needle, stylet and needle guard. The guard has a friction fit with the distal end of the needle and stylet to retain the guard. When in use, the guard is transferred to the hub end of the needle to interfit with a proximal end of the needle and serve as a guide for a guidewire to be projected through the needle.

2 Claims, 2 Drawing Sheets

COMBINED NEEDLE PROTECTOR AND GUIDEWIRE FEEDER

FIELD OF INVENTION

Needle cannula and guidewire placement for percutaneous penetration.

BACKGROUND AND OBJECTS OF THE INVENTION

Numerous medical procedures in present practice involve the placement of guidewires in veins or arteries of the human body. This procedure requires percutaneous penetration into the blood vessel and introduction of a sterile guidewire into the vessel. The wire serves to guide the introduction of a suitable catheter into the vessel after penetration has been achieved.

The guidewires used may have a straight end or what is called a J-end. The latter end presents a curved profile within a vessel and facilitates deep penetration especially around curves or turns in the vessel.

In many cases the penetrating stylet is contained in a needle which is also projected into the vessel to serve as a guide for the guidewire which is introduced through the lumen of the needle.

It is an object of the present invention to provide a combined stylet and needle with a manipulative hub or both. A needle and stylet end protector is provided to facilitate handling of the combination prior to use. The protector is then removable and insertable into the hub of the needle to serve as a guide for the introduction of a guidewire into the needle and ultimately into the penetrated vessel. The protector will facilitate the introduction of either a straight end or J-end of a guidewire since it can act as a straightener for the J-end to allow passage through the needle prior to entry into the penetrated vessel.

Other objects and features of the invention will be apparent in the following description and claims in which the principles of the invention are set forth together with details to enable persons skilled in the art to which the invention pertains to practice the invention all in connection with the best mode presently contemplated for the invention.

BRIEF DESCRIPTION OF THE DRAWINGS

Drawings accompany the disclosure and the various views thereof may be briefly described as.

DETAILED DESCRIPTION OF THE INVENTION AND THE MANNER AND PROCESS OF USING IT

Figure 1:
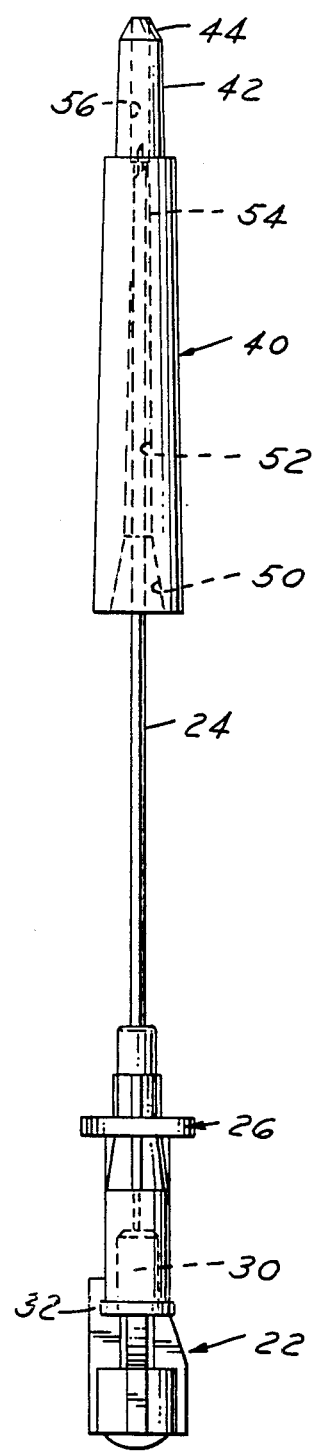
FIG. 1, a view of a needle-stylet assembly with needle protector in place.
Figures 2, 3:
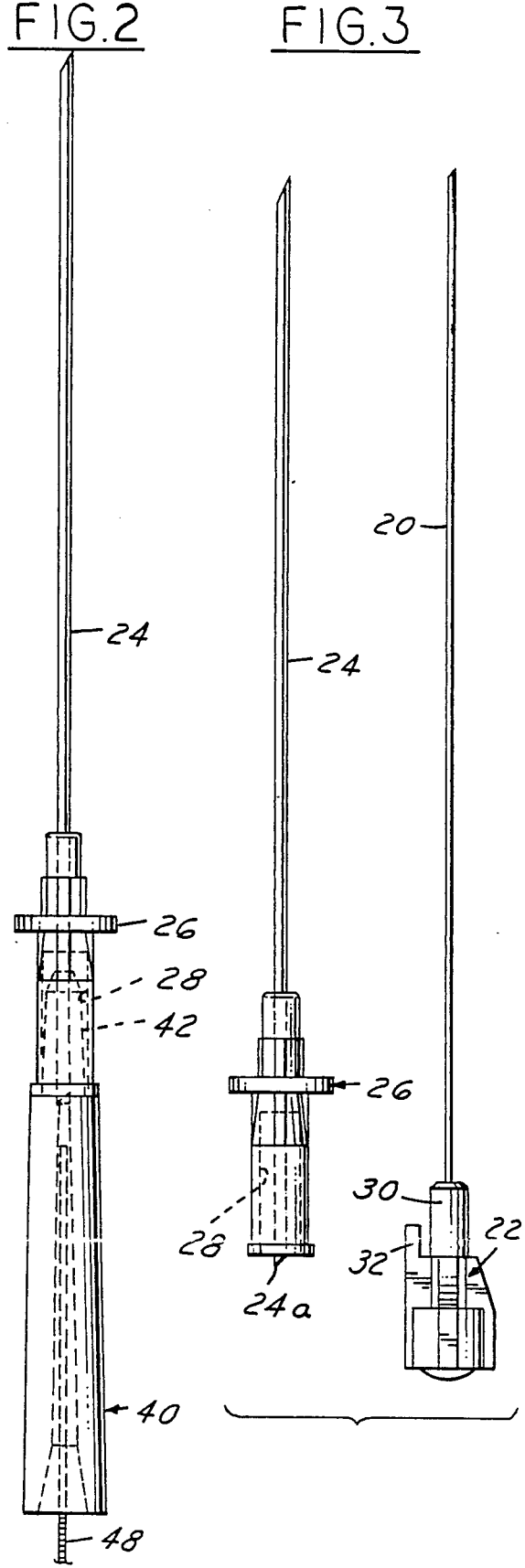
FIG. 2, a view of the needle and needle hub with the needle protector in the guide position.
FIG. 3, a combined view of the stylet and needle disassembled.

With reference to the drawings, in FIGS. 1, 2 and 3, the elements of the invention are illustrated. In FIG. 3, a stylet 20 having a hub 22 is illustrated adjacent a needle 24 having a lumen to receive the stylet 20. A hub 26 mounts the needle 24. The hub 26 has an end recess 28 to receive a central projection 30 on stylet hub 22. A small axial projection 32 interfits with a suitable notch in the outer end of hub 28 to facilitate simultaneous manipulation of the stylet and needle.

Figure 4:
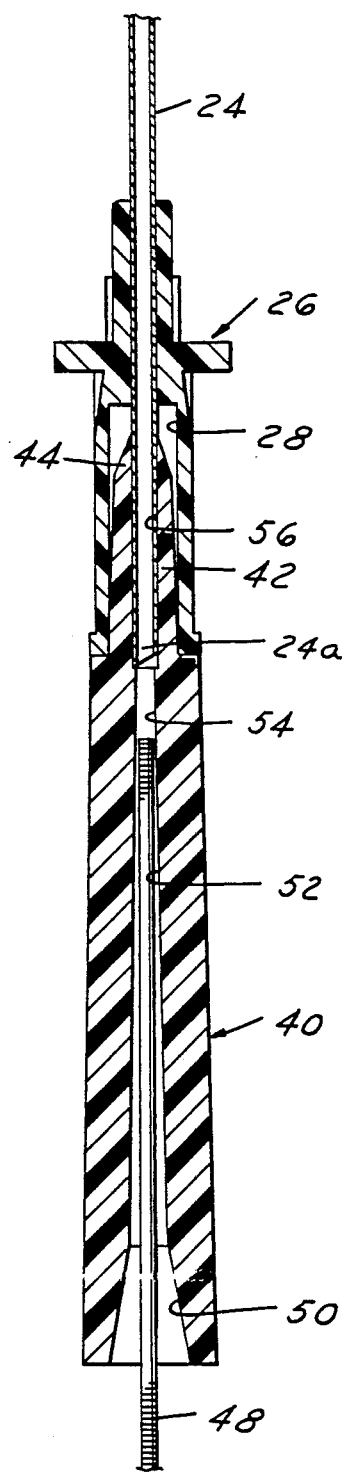
FIG. 4, an enlarged sectional view of the needle hub and protector-guide in the guide position.
Figure 5:
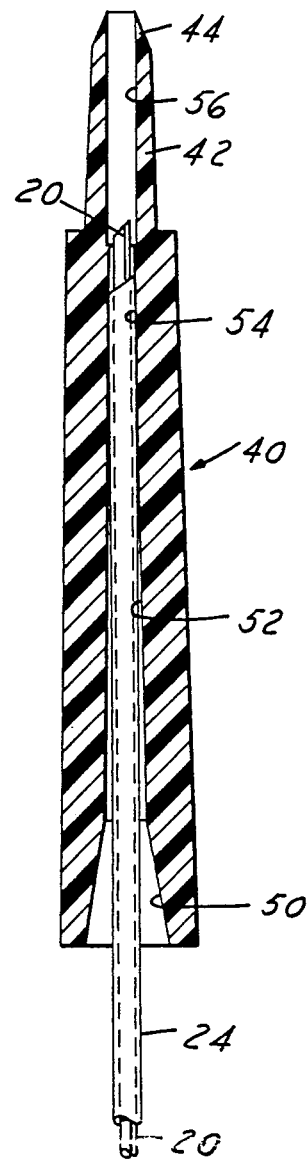
FIG. 5, an enlarged sectional view of the protector-guide in the protection position.

In FIGS. 1 and 2, a combination needle protector and guidewire feeder element is illustrated at 40. In FIG. 1, the element 40 is in a needle protection position wherein, as shown in FIG. 5, the needle 24 containing the stylet 20 is forced into a friction fit in the guard. The element 40 has a reduced end projection 42 with a tapered end 44. In FIG. 2, the element 40 is shown in the guide position with the portion 42 interfitted into the recess 28. FIGS. 4 and 5 illustrate these positions in enlarged sectional views.

It will be noted, in FIGS. 2, 3 and 4, that the proximal end of the needle 24 extends through the hub 26 and projects slightly beyond the end of the hub at 24a, FIG. 3.

The guard-guide 40, as illustrated in FIG. 1, has a central passage with three distinct axially spaced portions. The first portion 50 is tapered from the open end to a second longer tapering portion 52 which originates at the base of portion 50 and tapers to an end area 54 which is slightly smaller than the diameter of the needle 24. The third portion 56 within the projecting portion 42 has a diameter to readily receive the needle diameter 24. Thus, when the needle 24 and included stylet are thrust into the guard, there will be a friction fit which retains the guard on the assembly. However, when the guard is applied as in FIG. 2, the proximal end of needle 24 will readily fit into the recess 56.

In the operation of the combination illustrated and described above, the combined elements of the combination are sold and packaged as shown in FIG. 1 with the point guide-guard 40 carried frictionally on the needle 24. The end of the stylet 20 is protected within the guard 40. See also the enlarged view in FIG. 5.

When the combination is removed from the sterile package in which it is shipped, the protector element 40 is removed and the needle-stylet assembly is used to perforate the skin and vessel of a patient. The stylet is then withdrawn from the needle. There may be blood issuing from the needle at this time. With the stylet removed, the end 42 of the guard element 40 is inserted into the recess 28 of the hub 26 of needle 24.

Figure 6:
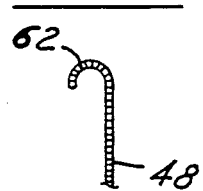
FIG. 6, a view of a guidewire with a J-end.

At this time, a guidewire 48, FIG. 6, is selected for entry into the recess 42 of the needle and the perforated vessel. The passage 54, 56 aligns with the proximal end 24a of needle 24 and the guidewire may be readily threaded through passage 50, 52, 54 and 56 into the lumen of needle 24 and then into the blood vessel. If the surgeon desires to utilize the J-end 62 of the guidewire, the end will be straightened temporarily and fed into the passage 50, 52 where it will remain straight as fed into and through the lumen of needle 24. As the J-end leaves the needle and enters the vessel, it will return to the J-shape and progress forward in this fashion.

Thus, the guard-guide element 40 serves as initial protection for the sterilized stylet and needle, and when removed, can selectively be installed as the guide for the guidewire into the needle lumen.

What is claimed is:

1. A combination for assisting in the insertion of a guidewire into a vessel which comprises:
    (a) a needle hub with an attached percutaneous needle having a lumen for feeding a guidewire into a vessel, said needle hub having a receiving recess at a proximal end, the proximal end of said needle extending centrally into said receiving recess, the recess having a dimension to provide a space between said extending needle and the inner wall of said recess, (b) a stylet hub with an attached stylet to be received in the lumen of said needle and having a portion on said stylet hub to be received in said recess of said needle hub during a percutaneous procedure, and (c) a combination protector guard and guidewire guide selectively usable as a guard and a guide which comprises a hollow quill having a central elongate passage to receive, enclose, and frictionally engage said needle when said needle is not being used, and having a projection portion usable selectively to insert into the space of said receiving recess around the proximal end of said needle, the elongate passage of said quill having a progressively decreasing dimension from the proximal end to the distal end to feed a guidewire from the proximal end to said needle lumen after removal of the stylet from a vessel.

2. A combination as defined in claim 1 in which said central passage of said quill is tapered from the proximal end to an ensmalled end having a diameter substantially equal to the inner diameter of said needle lumen.

* * * * *